United States Patent

Strong et al.

[11] Patent Number: 5,161,417
[45] Date of Patent: Nov. 10, 1992

[54] DUAL PHASE SAMPLER

[75] Inventors: Russell C. Strong, Richmond; J. Scott Walker, Missouri City, both of Tex.

[73] Assignee: Nalco Chemical Company, Naperville, Ill.

[21] Appl. No.: 604,574

[22] Filed: Oct. 26, 1990

[51] Int. Cl.$^5$ ............................................. G01N 1/00
[52] U.S. Cl. ............................. 73/863.86; 73/863.31
[58] Field of Search ..................... 73/863.81–863.86, 73/866.5, 863.80; 138/114

[56] References Cited

U.S. PATENT DOCUMENTS

| | | | |
|---|---|---|---|
| 3,085,435 | 4/1963 | Miscoe et al. | 73/863.31 |
| 3,552,211 | 1/1971 | Dollinger et al. | 73/863.24 |
| 4,009,739 | 3/1977 | Weatherford | 138/114 |
| 4,413,533 | 11/1983 | Diesel | 73/863.31 |
| 4,461,347 | 7/1984 | Layton et al. | 138/114 |

FOREIGN PATENT DOCUMENTS

| | | | |
|---|---|---|---|
| 0206825 | 12/1986 | European Pat. Off. | 138/114 |
| 1177715 | 9/1985 | U.S.S.R. | 73/863.86 |

OTHER PUBLICATIONS

Standard Practice for Sampling and Handling Cyclic Products, in Annual Book of ASTM Standards, D3437-78, pp. 786–790, Jan. 1979.

Standard Method of Sampling Liquidifed Petroleum (LP) Gases, in Annual Book of ASTM Standards, D1265-77, pp. 80–83, Aug. 1977.

Standard Test Method for Obtaining Hydrocarbon Fluid Samples Using a Floating Piston Cylinder, In Annual Book of ASTM Standards, D3700-78, pp. 398–402, Oct. 1978.

Standard Practice for Manual Sampling of Petroleum and Petroleum Products, in Annual Book of ASTM Standards, D4057-81, pp. 649–672, Oct. 1981.

Primary Examiner—Robert Raevis
Attorney, Agent, or Firm—Arnold, White & Durkee

[57] ABSTRACT

To obtain two or more fluid samples simultaneously, a sampling probe is provided which has an outer tube coaxially disposed about an inner tube. The ends of the inner tube and outer tube are typically spaced apart longitudinally, so that they may be positioned at different locations within a pipeline. Fluid flows through the inner tube and through the annulus formed between the inner tube and the outer tube. The fluid is then withdrawn from the inner tube and from the annulus for testing.

12 Claims, 4 Drawing Sheets

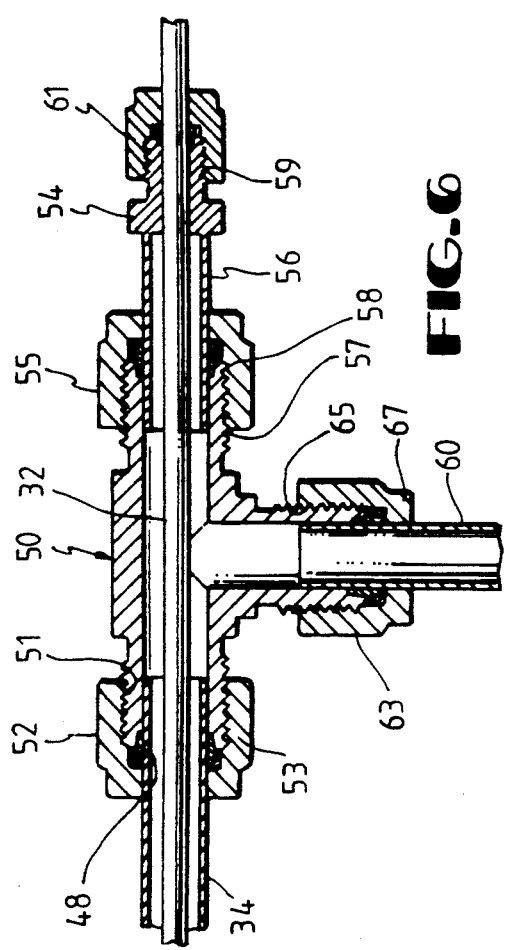
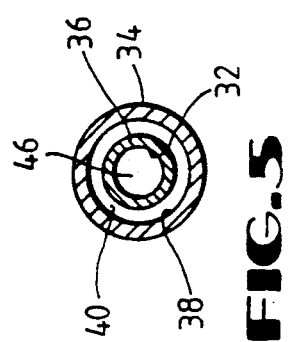
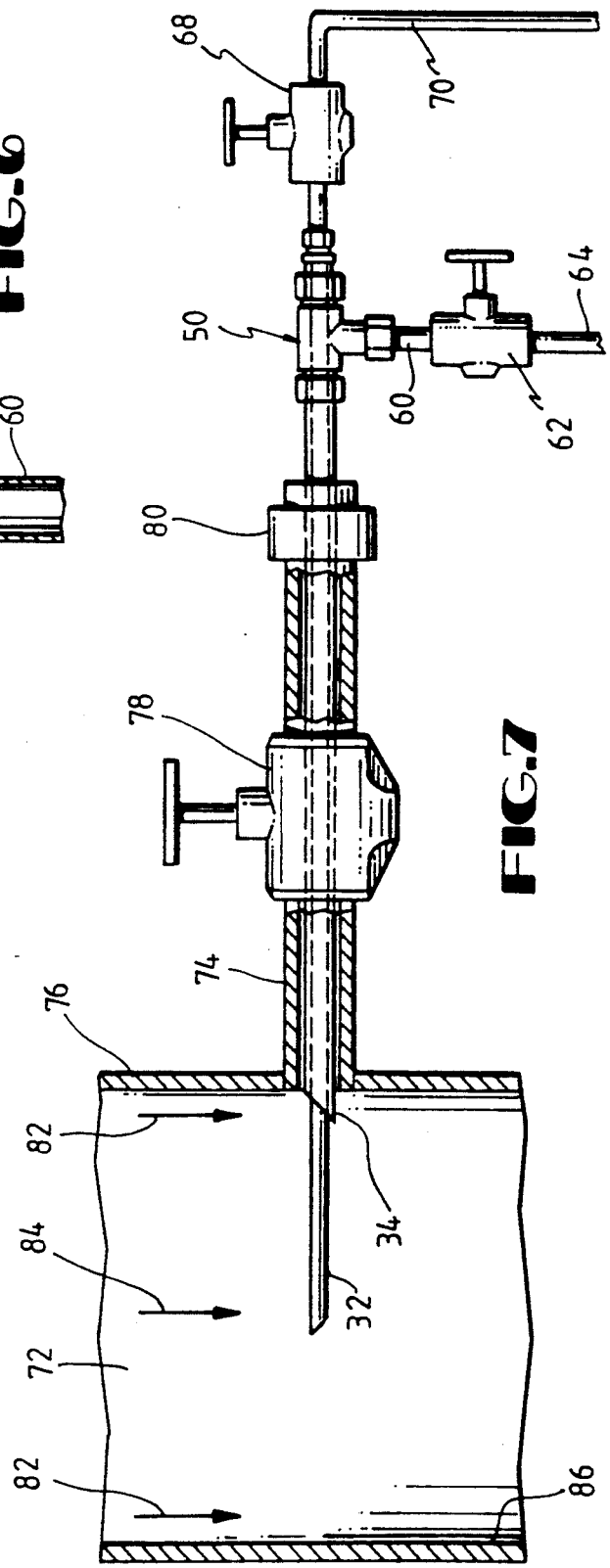

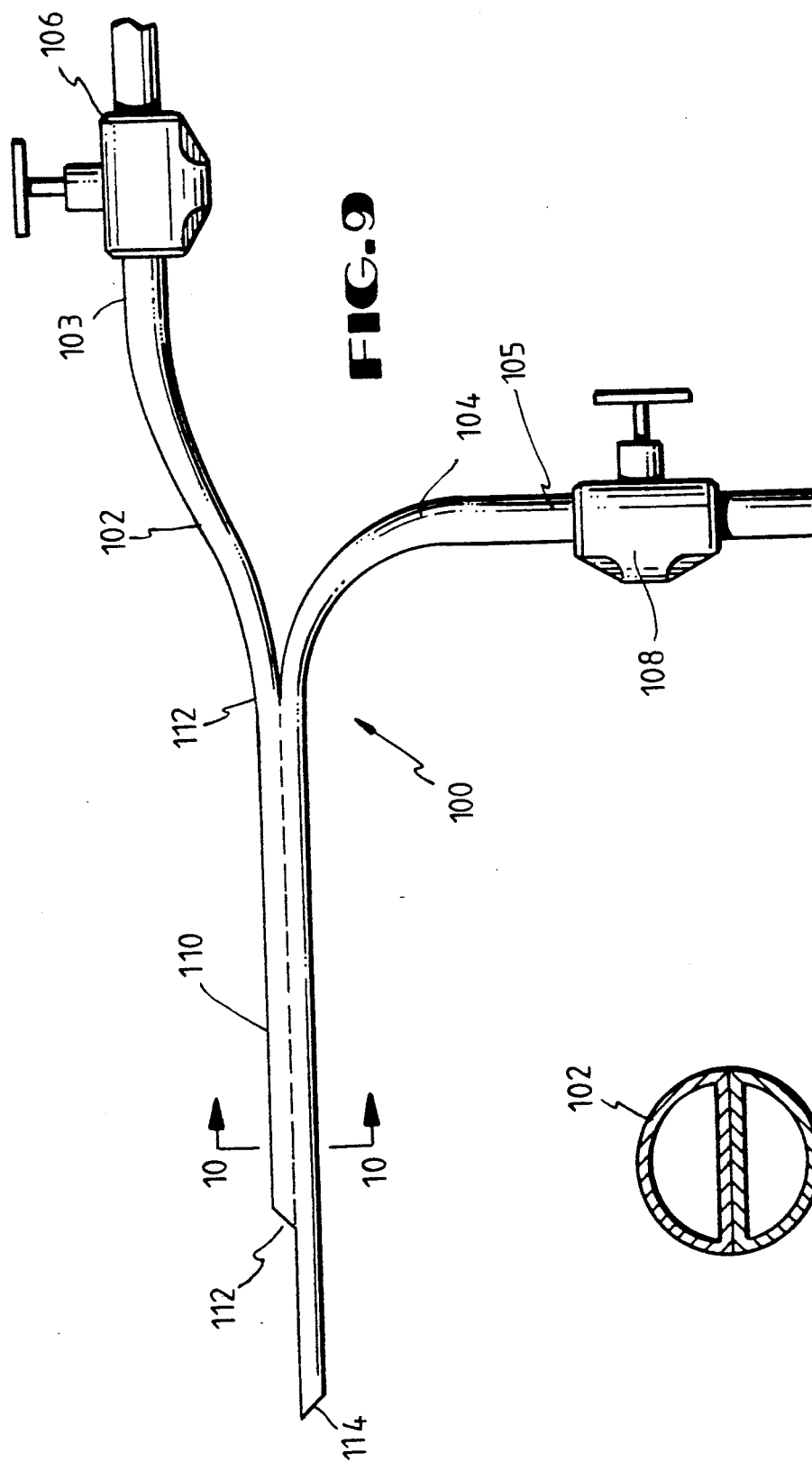

DUAL PHASE SAMPLER

BACKGROUND OF THE INVENTION

1. Field of the Invention

This invention relates generally to the sampling of petroleum and petroleum products, and, more particularly, to an apparatus for simultaneously sampling a stream of petroleum or petroleum products in at least two positions within the stream.

2. Description of the Related Art

During the refinement of petroleum and petroleum products, process engineers use various test methods to determine the physical and chemical characteristics of the products. These physical and chemical characteristics indicate whether the products are being processed as the engineers had planned. Quite often, the test results point to problems in the refinement process, such as corrosion or the improper mixture of chemical additives. In addition, the test results are also used for custody transfer and pricing determinations.

For the process engineers to make accurate determinations in view of the test results, the samples should be representative of the material or product being sampled. Whether the samples represent the sampled material depends upon the material being sampled; the tank, carrier, container or line from which the sample is obtained; the cleanliness of the sample container; and the sampling procedure used. Ideally, process engineers obtain a sample from various locations in the tank or container so that the samples will be representative of the material being sampled. Designation D 4057-81 of the ASTM standards describes various sampling methods and apparatuses which may be used in an effort to achieve these representative test results.

To sample a semiliquid material in a pipeline, a filling line, or a transfer line, process engineers prefer to use a continuous automatic sampling method. One preferred automatic sampling method employs a sampling probe that is inserted into the stream flowing within the pipeline. Ideally, the probe is inserted into a portion of the stream that is representative of the entire stream. FIGS. 1-3 illustrate various commonly used probe designs. FIG. 1 illustrates a tube 10 that extends to the center 14 of the pipeline 12. The tube 10 terminates at a bevelled angle, typically a 45° angle, so that the open tube 10 faces upstream. FIG. 2 illustrates a tube 18 having a bent end 20. The tube 18 is positioned with the end 20 at the center of the pipeline 12, so that the opening of the tube 18 faces upstream. FIG. 3 illustrates a closed-end tube 22 having a round orifice 24 spaced near the closed end. The tube 22 is positioned such that the orifice 24 is in the center of the pipeline 12 and facing upstream.

While the probes illustrated in FIGS. 1-3 were shown positioned in the center of the pipeline, a sampling probe cannot always be positioned in the center and still obtain a representative sample of the material in the stream. If a nonhomogeneous fluid is to be sampled, the location, position, and size of the probe may differ to minimize any separation of water and heavier particles that would make their concentration in the sample different from their concentration in the stream as a whole. In addition, section 9.4.3 of the above-mentioned ASTM standards lists a number of other considerations regarding probe location. For instance, the standards recommend that the probe should always be in a horizontal position to prevent drain-back of any part of the sample into the main stream. Preferably, the sampling probe should be located in a vertical run of pipe. However, if a vertical run is not available, a probe may also be located in a horizontal run of pipe provided the flowing velocity is high enough to provide adequate turbulent mixing. While adequate flowing velocity may not eliminate a concentration difference between the bottom of the pipe and the top of the pipe, it may provide an average concentration at the center of the pipe that will be representative of the concentration in the entire stream.

Of course there are other similar methods of retrieving a fluid sample from a pipeline. For instance, an outlet pipe can be connected in fluidic communication with the main pipeline. A valve controls the fluid flow through the outlet pipe. When a process engineer desires to sample the material within the main pipeline, the engineer places a container at the end of the outlet pipe, and opens the valve so that a sample flows from the main pipeline, through the outlet pipe, and into the container. However, since the outlet pipe does not extend into the main pipeline, the sample may not be representative of the material within the main pipeline.

In a semiliquid environment (vapor/liquid mix), it is often desirable to provide a water wash which is distributed uniformly in the pipeline to prevent the overhead of vapors from causing corrosion problems within the pipeline. In this situation, it is desirable to take a sample at various positions across the width of the pipeline. Therefore, a probe must be inserted into the pipeline at various locations. This is a time consuming task which requires careful measurement to be certain of the positioning of the tip of the probe.

The present invention is directed to over coming or at least minimizing, one or more of the problems set forth above.

SUMMARY OF THE INVENTION

In accordance with one aspect of the present invention, there is provided a fluid sampling apparatus. The apparatus includes a first hollow member which has a first inner surface and a first outer surface. A second hollow member has a second inner surface and a second outer surface and is disposed about the first member. Thus, a fluid path through second hollow member between the first outer surface and the second inner surface is formed. Two samples are obtained by withdrawing fluid from the first hollow member and from the fluid path separately.

In accordance with the present invention, at least two fluid samples can be simultaneously obtained from a pipeline. The first end of a first tube is positioned at a first predetermined location within the pipeline, and the first end of a second tube, which is coaxially disposed about the first tube, is positioned at a second predetermined location within the pipeline. Then, a first fluid sample is withdrawn through the first tube, and a second fluid sample is withdrawn through the second tube. Preferably, the rate at which the first fluid sample is withdrawn through the first tube, and the rate at which the second fluid sample is withdrawn through the second tube, is controlled, for instance, by the use of valves.

BRIEF DESCRIPTION OF THE DRAWINGS

The foregoing and other advantages of the invention will become apparent upon reading the following detailed description and upon reference to the drawings in which:

FIG. 5 is a cross-sectional view of the sampling probe along line 5—5 in FIG. 4;

FIG. 6 is a detailed cross-sectional view of a T-shaped fitting;

FIG. 7 illustrates the sampling probe of FIG. 4 inserted into a pipeline to obtain two samples of the material within the pipeline;

FIG. 9 illustrates an alternate embodiment of a sampling probe in accordance with the present invention; and FIG. 10 is a cross-sectional view of the sampling probe of FIG. 9 taken along line 10—10.

Figure 1:
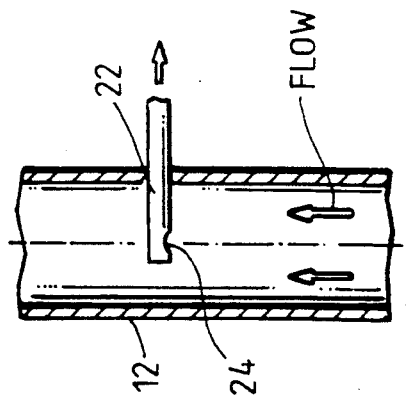
FIG. 1 illustrates a prior art probe having a bevelled end positioned within a pipeline.

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives following within the spirit and scope of the invention as defined by the appended claims.

DESCRIPTION OF THE PREFERRED EMBODIMENTS

Figure 4:
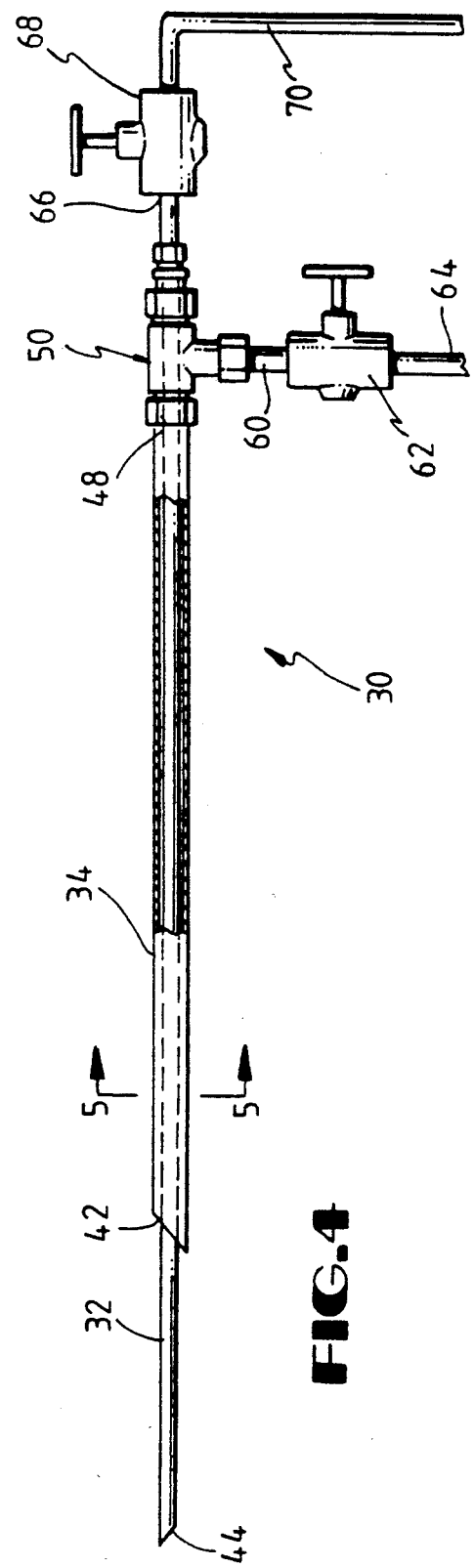
FIG. 4 illustrates a dual sampling probe in accordance with the present invention.

Turning now to the drawings and referring initially to FIG. 4, a fluid sampler is illustrated and generally designated by the reference numeral 30. The fluid sampler 30 includes an inner tube 32 and an outer tube 34. As illustrated in FIG. 5, the outer tube 34 is coaxially disposed about the inner tube 3 such that the inner surface 38 of the outer tube 34 is spaced apart from the outer surface 36 of the inner tube 32. The space defined between the inner tube 32 and the outer tube 34 forms an annulus 40.

Figure 8:
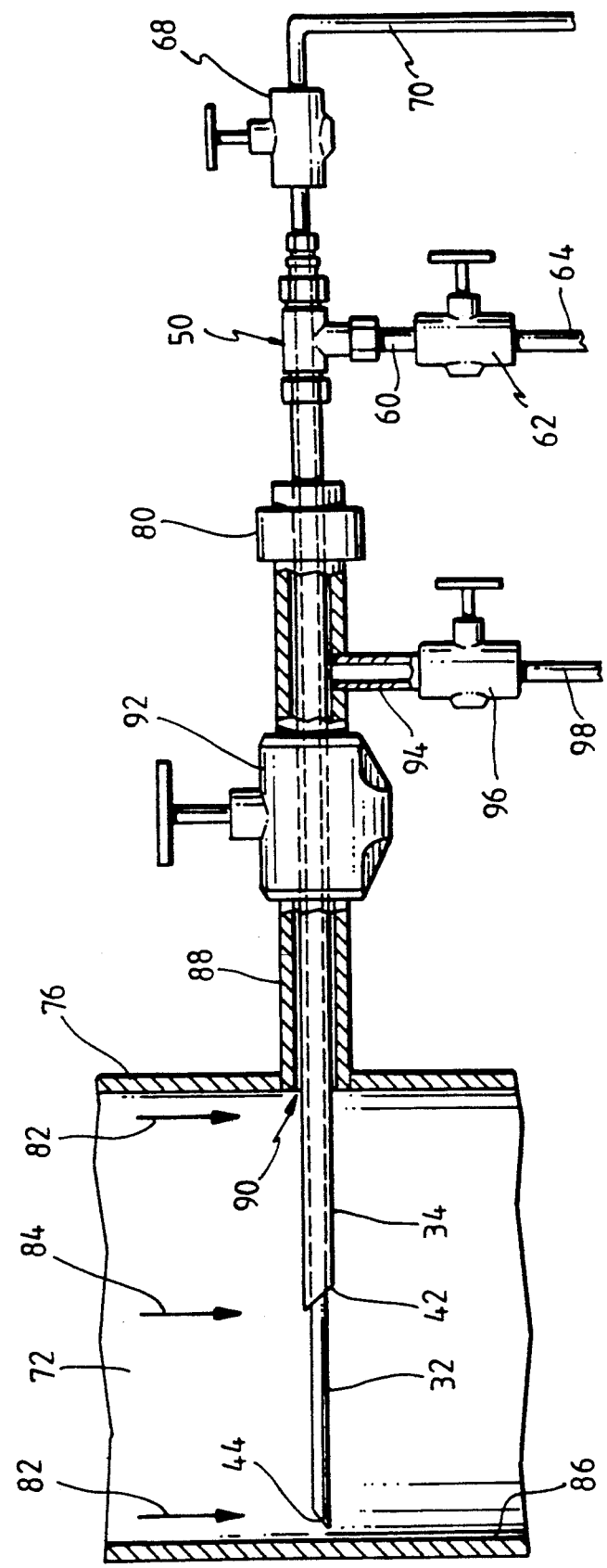
FIG. 8 illustrates the sampling probe of FIG. 4 inserted into a pipeline for obtaining three samples of the material within the pipeline.

Preferably, the inner tube 32 extends longitudinally outwardly from the end 42 of the outer tube 34. The distance between the end 44 of the inner tube 32 and the end 42 of the outer tube 34 is selected depending on the size of the pipeline and on the type of sample to be taken from the pipeline. Moreover, the overall length of the tubes 32 and 34 is preferably long enough so that the end 44 of the inner tube 32 can reach the far wall of the pipeline 72 so that the sampler 30 may be used to take a variety of samples. Two positions are illustrated in FIGS. 7 and 8.

Figure 2:
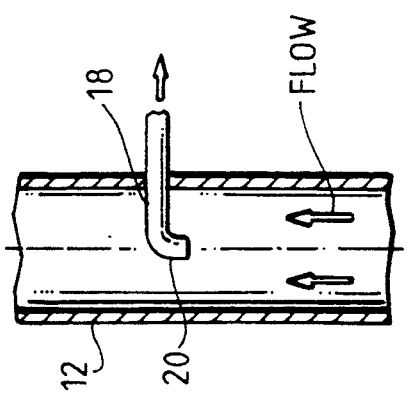
FIG. 2 illustrates a prior art probe having a bent end positioned with a pipeline.
Figure 3:
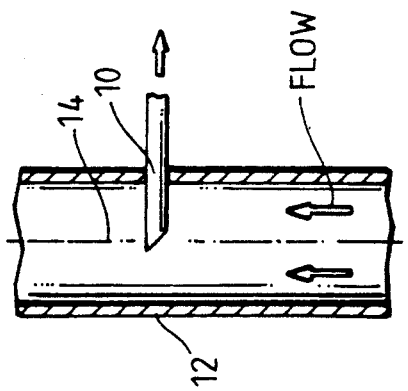
FIG. 3 illustrates a prior art probe having an orifice in the end thereof positioned within a pipeline.

To facilitate the sampling of certain fluids, the end 42 of the outer tube 34 is cut at an angle so that the annulus 40 faces upwardly, as illustrated in FIG. 4. The end 44 of the inner tube 32 is also cut at an angle so that the opening 46 of the inner tube 32 faces downwardly. However, both ends 42 and 44 may be cut so that the opening 46 and the annulus 40 face in the same direction or in opposite directions, depending upon the type and flow characteristics of the fluid being sampled. For instance, when sampling a gas, the openings of the tubes 32 and 34 generally faces downstream, and when sampling a liquid, the openings of the tubes generally face upstream. Additionally, the end 44 of the inner tube 32 could take the form of the end 20 in FIG. 2 or of the end 24 in FIG. 3 in a particular application.

To withdraw the fluid from the annulus 40, the other end 48 of the outer tube 34 is connected to a T-shaped fitting 50. Preferably, the end 48 of the outer tube 34 is attached to the T-shaped fitting 50 using a compression fit. First, the end 48 of the outer tube 34 slides into a ferrule 51 which forms one leg 52 of the fitting 50, as illustrated in FIG. 6. Then, a nut 53 is tightened onto the ferrule 51 so that the ferrule 51 tightly grips the end 48 of the outer tube 34.

The inner tube 32 extends through the legs 52 and 55 of the T-shaped fitting 50. To prevent fluid in the annulus 40 from exiting through the opposite leg 55 of the T-shaped fitting 50, the end 56 of a reducer 54 is clamped into a ferrule 57 that forms the opposite leg 55 by tightening a nut 58 onto the ferrule 57. The inner tube 32 slides through a ferrule 59 of the reducer 54. Then, a nut 61 is tightened onto the ferrule 59 to clamp the inner tube 32 in the ferrule 59.

The lower leg 63 of the T-shaped fitting 50 is connected to one end of a tube 60. Again, the end of the tube 60 is preferably attached to a ferrule 65 that forms the lower leg 63 by tightening a nut 67 onto the ferrule 65. The other end of the tube 60 is connected to valve 62. Preferably, the valve 62 is a metering valve so that fluid may be withdrawn from the annulus 40 at various selected rates. A tube 64, which is connected to the valve 62, carries the sample to an appropriate container (not shown).

To withdraw the fluid from the inner tube 32, after it passes through the fitting 50, the end 66 of the inner tube 32 is connected to a valve 68. Preferably, the valve 68 is also a metering valve so that fluid may be withdrawn from the tube 32 at various selected rates. A tube 70, which is connected to the valve 68, delivers the fluid sample to an appropriate container (not shown).

Referring now to FIG. 7, to obtain a fluid sample using the process sampler 30, the sampler 30 is inserted into a pipeline 72. Preferably, an outlet pipe 74 is joined to a wall 76 of the pipeline 72. The inner diameter of the outlet pipe 74 is large enough to accommodate the outer diameter of the outer tube 34. Since it is often desirable to insert the sampler 30 into the pipeline 72 while fluid is flowing through the pipeline 72, a gate valve 78 is inserted in the outlet pipe 74 to selectively open or close the outlet pipe 74. A packing gland 80 is fitted to the other end of the outlet pipe 74. To inset the sampler 30 into the pipeline 72, the ends 42 and 44 of the sampler 30 are inserted through the packing gland 80 while the valve 78 remains closed. Then, the valve 78 is opened, and the ends 42 and 44 of the sampler 30 are inserted through the valve 78 and into the pipeline 72. The packing gland 80 prevents fluid from escaping from the outlet pipe 74 while the sampler 30 takes samples.

As illustrated, the end 44 of the inner tube 32 is positioned at the center line of the pipeline 72. The end 42 of the outer tube 34 is positioned near the wall 76 of the pipeline 72. Therefore, fluid flowing through the opening 46 represents material taken from the center of the pipeline 72, while fluid flowing through the annulus 40 represents fluid flowing along the wall 7 of the pipeline 72. In this position, the sampler 30 is adapted to sample a process stream having a vapor component and a liquid component. The liquid flows in the direction of the arrow 82 and into the upwardly facing annulus 40. The vapor flows in the direction of the arrow 84 and into the oppositely facing opening 46 of the inner tube 32. Of course, if the arrow 84 also represented liquid flow, the end 44 of the inner tube 32 would be angled in the same direction as the end 42 of the outer tube 34.

The sampler 30 can also be used to obtain three samples simultaneously. As illustrated in FIG. 8, liquid samples are desired from the near wall 76 of the pipeline 72 and from the far wall 86 of the pipeline 72, while a vapor sample is desired from the center of the pipeline 72. To retrieve a liquid sample from the far wall 86, the sampler 30 is inserted so that the end 44 of the inner tube 32 is positioned adjacent the far wall 86. The distance between the end 44 of the inner tube 32 and the end 42 of the outer tube 34 is selected so that the end 42 is positioned at the center line of the pipeline 72. Since the inner tube 32 is detecting liquid flow, the end 44 is bevelled so that the opening 46 faces upstream. Similarly, since the outer tube 34 is sampling vapor flow, the end 42 is bevelled so that the annulus 40 faces downstream.

To detect the liquid flowing along the near wall 76, the inner diameter of the outlet pipe 88 is sized so that an annulus 90 is formed when the outer tube 34 is inserted through the outlet pipe 88. Like the configuration shown in FIG. 7, a gate valve 92 is disposed in the outlet pipe 88 to prevent fluid flow through the outlet pipe 88 when the sampler 36 is being inserted or retracted from the pipeline 72. Downstream from the gate valve 92, a sampling pipe 94 joins the outlet pipe 88 and fluidically communicates with the annulus 90. The sampling pipe 94 is connected to a metering valve 96, which in turn in connected to an outlet tube 98. Therefore, a fluid sample from the wall 76 can be withdrawn through the annulus 90 at various selected rates using the metering valve 96. Preferably, the tube 98 delivers the sampled fluid to an appropriate container (not shown).

It should be understood that the sampling device 30 is not limited to obtaining only two or three simultaneous samples. For instance, the sampling device 30 could be composed of three or more coaxially disposed tubes which would define two or more fluid-carrying annuluses. Moreover, the fluid may enter the tubes in any appropriate manner, whether through the ends of the tubes or through apertures along the length of the tubes. Furthermore, the fitting 50, described in detail with respect to FIG. 6, need not be a separate unit. For instance the tubes 32 and 34 may be molded to form an integral fitting that routes fluid from the inner tube to a first container and fluid from the annulus to a second container.

Referring now to FIGS. 9 and 10, an alternate embodiment of a sampling probe is generally designated by a reference numeral 100. The probe 100 includes a first tube 102 and a second tube 104. The ends 103 and 105 of each respective tube 102 and 104 are connected to a respective valve 106 and 108. Preferably, the valves 106 and 108 are metering valves for controlling the rate o fluid flow through the respective tubes 102 and 104. To facilitate attachment of the tubes 102 and 104 to the respective valves 106 and 108, the ends 103 and 105 of the tubes 102 and 104 are preferably circular in cross-sectional shape.

To form the sampling end 110 of the probe 100, the tubes 102 and 104 are joined at a junction 112. Since the sampling probe 100 is used in the same manner as the sampling probe 30, preferably the sampling end 110 of the probe 100 has a circular cross-sectional shape so that the sampling end 110 may be inserted through a conventional packing gland, such as the packing gland 80. Therefore, the sampling end 110 of each tube 102 and 104 preferably exhibits a semicircular cross-sectional shape, as illustrated in FIG. 10. The semicircular cross-section may be formed, for instance, by cutting both tubes 102 and 104 longitudinally and affixing a flat plate to one or both tubes, or by molding the tubes 102 and 104 into a semicircular shape at the sampling end 110. The tubes 102 and 104 are then attached to one another longitudinally in any suitable manner, such as by gluing or welding.

To take a fluid sample from two different locations in a pipeline, the ends 112 and 114 of each respective tube 102 and 104 at the sampling end 110 are separated by a predetermined longitudinal distance. As illustrated, the end 112 of the tube 102 is angled upwardly, and the end 114 of the tube 104 is angled downwardly. Therefore, if the probe 100 were inserted into the pipeline 76 instead of the probe 30, as illustrated in FIG. 7, the end 112 would collect a liquid sample and the end 114 would collect a vapor sample.

We claim:

1. A fluid sampling system, comprising:
a pipeline carrying fluid to be sampled;
a first hollow member having a first inner surface and a first outer surface and having a first end and a second end;
a second hollow member having a second inner surface and a second outer surface and being disposed about said first member, thereby forming a fluid path through said second hollow member between said first outer surface and said second inner surface, said second member also having a first end and a second end, said first end of said first hollow member extending outwardly from said first end of said second hollow member, thereby adapting said first end of said first member to be positioned at a first predetermined location within said pipeline and said first end of said second member to be positioned at a second predetermined location within said pipeline; and
means for withdrawing fluid from said first hollow member and from said fluid path separately.

2. The system, as set forth in claim 1, wherein:
said withdrawing means comprises a fitting being connected to said second end of said second member to provide fluid communication with said fluid path.

3. The system, as set forth in claim 2, further comprising:
means for variably controlling fluid flow through said first member; and
means for variably controlling fluid flow through said fluid path.

4. The system, as set forth in claim 3, wherein:
said means for variably controlling fluid flow through said first member comprises a first metering valve being operably connected to control fluid flow through said first member; and
said means for variably controlling fluid flow through said second member comprises a second metering valve being operably connected to control fluid flow through said second member.

5. A fluid sampling system, comprising:
a pipeline carrying fluid to be sampled;

a first hollow tube having a first inner diameter and a first outer diameter and having a first end and a second end;

a second hollow tube having a second inner diameter and a second outer diameter and being coaxially disposed about said first tube, said second inner diameter being greater than said first outer diameter, thereby forming an annulus between said first tube and said second tube, said second hollow tube also having a first end and a second end, said first end of said first tube extending outwardly from said first end of said second tube, thereby adapting said first end of said first tube to be positioned at a first predetermined location within said pipeline and said first end of said second tube to be positioned at a second predetermined location within said pipeline;

means for withdrawing fluid from only said first tube; and means for withdrawing fluid from only said annulus.

6. The system, as set forth in claim 5, wherein:
said means for withdrawing fluid from only said annulus comprises a fitting being connected to said second end of said second tube to provide fluid communication with said annulus.

7. The system, as set forth in claim 6, further comprising:
means for variably controlling fluid flow through said first tube; and
means for variably controlling fluid flow through said annulus.

8. The system, as set forth in claim 7, wherein:
said means for variably controlling fluid flow through said first tube comprises a first metering valve being operably connected to control fluid flow through said first tube; and
said means for variably controlling fluid flow through said annulus comprises a second metering valve being operably connected to control fluid flow through said second tube.

9. The system, as set forth in claim 5, wherein:
said first end of said first tube is formed to sample fluid having a first particular phase; and
said first end of said second tube is formed to sample fluid having a second particular phase.

10. A fluid sampling system, comprising:
a pipeline carrying fluid to be sampled;
a first hollow tube having a first inner diameter and a first outer diameter and having a first end and a second end;
a second hollow tube having a second inner diameter and a second outer diameter and having a first end and a second end, said second tube being coaxially disposed about said first tube and said second inner diameter being greater than said first outer diameter, thereby forming an annulus between said first tube and said second tube;
said first end of said first tube extending longitudinally outwardly from said first end of said second tube, thereby adapting said first end of said first tube to be positioned at a first predetermined location within said pipeline and said first end of said second tube to be positioned at a second predetermined location within said pipeline;
a fitting being connected to said second end of said second tube and providing fluid communication with said annulus;
a first valve being connected to said fitting, said first valve controlling the rate of fluid flow through said annulus; and
a second valve being connected to said second end of said first tube, said second valve controlling the rate of fluid flow through said first tube.

11. The system, as set forth in claim 10, wherein:
said first end of said first tube is formed to sample fluid having a first particular phase; and
said first end of said second tube is formed to sample fluid having a second particular phase.

12. The system, as set forth in claim 10, wherein:
said first tube passes through said fitting.

* * * * *

UNITED STATES PATENT AND TRADEMARK OFFICE
CERTIFICATE OF CORRECTION

PATENT NO. : 5,161,417
DATED : November 10, 1992
INVENTOR(S) : Russell C. Strong, J. Scott Walker It is certified that error appears in the above-indentified patent and that said Letters Patent is hereby corrected as shown below:

Column 1, line 46, "open" should be --opening of the--.

Column 3, line 43, "3" should be --32--.

Column 4, line 65, "7" should be --76--.

Column 5, line 4, "84" should be --44--.

Column 5, line 16, "42" should be --44--.

Column 5, line 60, "o" should be --of--.

Signed and Sealed this

Nineteenth Day of October, 1993

Attest:

BRUCE LEHMAN

*Attesting Officer*   *Commissioner of Patents and Trademarks*